(12) United States Patent
Fujiwara et al.

(10) Patent No.: US 9,347,031 B2
(45) Date of Patent: *May 24, 2016

(54) CONTAINER FOR FORMING A CELL AGGREGATE AND A METHOD FOR FORMING A CELL AGGREGATE

(75) Inventors: Shigeyoshi Fujiwara, Kanagawa (JP); Keigo Takei, Kanagawa (JP); Aya Hirayama, Kanagawa (JP); Yukimitsu Suda, Tokyo (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 132 days.

This patent is subject to a terminal disclaimer.

(21) Appl. No.: 13/377,850

(22) PCT Filed: Jun. 15, 2010

(86) PCT No.: PCT/JP2010/060142
§ 371 (c)(1),
(2), (4) Date: Dec. 13, 2011

(87) PCT Pub. No.: WO2010/147122
PCT Pub. Date: Dec. 23, 2010

(65) Prior Publication Data
US 2012/0156696 A1    Jun. 21, 2012

(30) Foreign Application Priority Data
Jun. 15, 2009 (JP) ................. 2009-142254

(51) Int. Cl.
| | | |
|---|---|---|
| *G01N 33/53* | (2006.01) | |
| *C12M 1/00* | (2006.01) | |
| *G01N 33/50* | (2006.01) | |
| *C12N 5/0793* | (2010.01) | |
| *C12N 5/0775* | (2010.01) | |
| *C12N 5/09* | (2010.01) | |
| *C12N 5/071* | (2010.01) | |

(52) U.S. Cl.
CPC .............. *C12M 23/20* (2013.01); *C12N 5/062* (2013.01); *C12N 5/0667* (2013.01); *C12N 5/0671* (2013.01); *C12N 5/0693* (2013.01); *G01N 33/5082* (2013.01); *C12N 2533/30* (2013.01)

(58) Field of Classification Search
CPC .... C12N 5/062; C12N 5/0068; C12N 5/0667; C12N 5/0693; C12N 5/0671; C12N 2533/30; G01N 33/5082; C12M 23/20
See application file for complete search history.

(56) References Cited

U.S. PATENT DOCUMENTS

| 7,648,833 | B2 * | 1/2010 | Kurosawa et al. | 435/283.1 |
|---|---|---|---|---|
| 2005/0019801 | A1 * | 1/2005 | Rubin et al. | 435/6 |
| 2007/0181503 | A1 | 8/2007 | Maeno et al. | |
| 2007/0241054 | A1 | 10/2007 | Miyazawa et al. | |
| 2008/0300369 | A1 | 12/2008 | Suda et al. | |
| 2008/0300375 | A1 | 12/2008 | Suda et al. | |
| 2009/0156741 | A1 | 6/2009 | Suda et al. | |
| 2010/0113817 | A1 | 5/2010 | Miyazawa et al. | |
| 2012/0034709 | A1 * | 2/2012 | Maeno | 436/501 |
| 2012/0156696 | A1 * | 6/2012 | Fujiwara et al. | 435/7.21 |

FOREIGN PATENT DOCUMENTS

| EP | 1657302 | 5/2006 |
|---|---|---|
| EP | 1690867 | 8/2006 |
| EP | 2261274 | 12/2010 |
| EP | 2405267 | 1/2012 |
| JP | 64-054379 | 3/1989 |
| JP | 64-054380 | 3/1989 |
| JP | 64-054381 | 3/1989 |
| JP | 06-046831 | 2/1994 |
| JP | 06-153905 | 6/1994 |
| JP | 07-184990 | 7/1995 |
| JP | 11-302129 | 11/1999 |
| JP | 2004-290111 | 10/2004 |
| JP | 2006-007203 | 1/2006 |
| JP | 2006-007204 | 1/2006 |
| JP | 2006-011380 | 1/2006 |
| JP | 2006-011381 | 1/2006 |
| JP | 2006-011383 | 1/2006 |
| JP | 2006-204232 | 8/2006 |
| JP | 2008-017839 | 1/2008 |
| JP | 2008-061609 | 3/2008 |
| JP | 2008-174491 | 7/2008 |

(Continued)

OTHER PUBLICATIONS

Definition of somatic cell from the Science Daily website http://www.sciencedaily.com/articles/s/somatic_cell.htm downloaded Oct. 1, 2013.*
English translation pf JP 2006-008987 downloaded from the JPO Jun. 14, 2014.*
Solomons, T.W. Graham. Organic Chemistry. second edition. (John Wiley & Sons: New York, NY) published in 1980, pp. 657-666, 711-712, 768-769, 774-777, 788-790 and 826-833.*
Solomons Organic Chemistry (John Wiley and Sons: New York) published in 1980 pp. 704, 705, 711 and 717.*
The extended European search report mailed Dec. 12, 2012.
International Search Report mailed on Jul. 27, 2010.

(Continued)

*Primary Examiner* — Susan Hanley
(74) *Attorney, Agent, or Firm* — IPUSA, PLLC

(57) ABSTRACT

A container for forming a cell aggregate is provided in which a group represented by a general formula of:

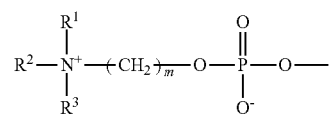

(in the formula, each of $R^1$, $R^2$, and $R^3$ is independently a an alkyl group with a carbon number of 1 or more and 6 or less and m is an integer of 2 or more and 6 or less.) and at least one of an amino group, a carboxyl group, and a hydroxyl group are present near a surface thereof.

3 Claims, 10 Drawing Sheets

(56) References Cited

FOREIGN PATENT DOCUMENTS

| JP | 2008-220205 | | 9/2008 |
|---|---|---|---|
| JP | 2009-050194 | | 3/2009 |
| WO | WO 2005001019 | A1 * | 1/2005 |
| WO | WO 2010101126 | A1 * | 9/2010 |
| WO | WO 2010147122 | A1 * | 12/2010 |

OTHER PUBLICATIONS

Aya Hirayama et al., "Development of materials modified with a novel phosphorylcholine coupler", Fine Chemical, Mar. 2009, vol. 38, No. 3, pp. 74 to 81.

Hiroshi Kurosawa et al., "Mouse ES Saibo no Haiyotai Keisei no Tameno Shinki Baiyo Gijutsu", University of Yamanashi, Faculty of Engineering Kenkyu Hokoku, 2003, vol. 52, pp. 23 to 29.

M. Muller et al., "Plasma aminofunctionalisation of PVDF microfiltration membranes: comparison of the in plasma modifications with a grafting method using ESCA and an amino-selective fluorescent probe", Surface and Coatingss Technology 116-119 (1999) 802-807.

Lidija Tusek et al., "Surface characterisation of NH3 plasma treated polyamide 6 foils", Colloids and Surfaces, A: Physicochemical and Engineering Aspects 195 (2001) 81-95.

Fabienne Poncin-Epaillard et al., "Reactivity of surface groups formed onto a plasma treated poly (propylene) film", Macromol. Chem. Phys. 200, 989-996 (1999).

European Office Action dated Feb. 17, 2016.

* cited by examiner

CD271

Nestin

CD271

CD133

CD133

PDGFRa

CD271

PDGFRb

CONTAINER FOR FORMING A CELL AGGREGATE AND A METHOD FOR FORMING A CELL AGGREGATE

TECHNICAL FIELD

The present invention relates to a container for forming a cell aggregate, a method for forming a cell aggregate, a cell aggregate, a method for screening a substance, and a method for exploring a cell function.

BACKGROUND ART

Conventionally, a cell aggregate is formed by culturing an adherent cell and a non-adherent cell.

Patent document 1 discloses a method for forming a neural stem cell aggregate in which a tissue including a pluripotent neural stem cell is suspended in a culture medium containing at least one kind of a stem cell growth factor and disseminated to and cultured in a container for forming a neural stem cell aggregate. Herein, the container for forming a neural stem cell aggregate has a non-aqueous cured coating layer on an inner surface thereof and is manufactured by coating an inner surface of a container with an aqueous resin to form an aqueous resin coating layer and subsequently curing the aqueous resin coating layer to be modified into an non-aqueous cured coating layer. Furthermore, a copolymer of 2-methacryloyloxyethylphosphorylcholine and another monomer (for example, butyl methacrylate, etc.) is illustrated for an aqueous resin.

However, when an adherent cell is cultured by such a container for forming a neural stem cell aggregate, adhesion of the adherent cell is inhibited by a non-aqueous cured coating layer, and as a consequence, the adherent cell is killed, which causes a problem that it is not possible to form a cell aggregate of adherent cells.

Patent document 1: Japanese Patent Application Publication No. 2008-220205

DISCLOSURE OF THE INVENTION

According to one aspect of the present invention, there is provided a container for forming a cell aggregate, wherein a group represented by a general formula of:

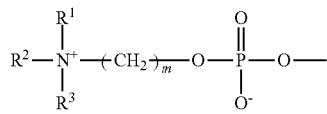

wherein each of $R^1$, $R^2$, and $R^3$ is independently an alkyl group with a carbon number of 1 or more and 6 or less and m is an integer of 2 or more and 6 or less, and at least one of an amino group, a carboxyl group, and a hydroxyl group are present at a surface thereof.

According to another aspect of the present invention, there is provided a method for forming a cell aggregate, wherein a somatic cell is cultured by using the container for forming a cell aggregate as described above to form a cell aggregate.

According to another aspect of the present invention, there is provided a method for screening a substance, including a step of culturing a somatic cell by using the container for forming a cell aggregate as described above to form a cell aggregate and a step of screening a substance by using the cell aggregate.

According to another aspect of the present invention, there is provided a method for exploring a cell function, including a step of culturing a somatic cell by using the container for forming a cell aggregate as described above to form a cell aggregate and a step of exploring a cell function by using the cell aggregate.

BEST MODE FOR CARRYING OUT THE INVENTION

Next, an embodiment for implementing the present invention will be described in conjunction with the drawings.

In a container for forming a cell aggregate in the present invention, a phosphorylcholine-like group represented by a general formula of:

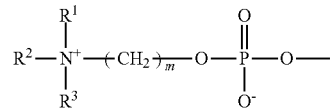

(in the formula, each of $R^1$, $R^2$, and $R^3$ is independently an alkyl group with a carbon number of 1-6 and m is an integer of 2-6.) and at least one of an amino group, a carboxyl group, and a hydroxyl group are present near a surface thereof.

Figure 1A:
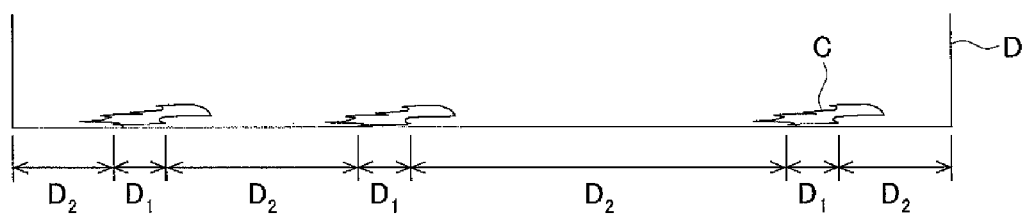
FIG. 1A is a diagram (part 1) illustrating one example of a method for forming a cell aggregate by using a container for forming a cell aggregate in the present invention.
Figure 1B:
FIG. 1B is a diagram (part 2) illustrating one example of a method for forming a cell aggregate by using a container for forming a cell aggregate in the present invention.

FIG. 1 illustrates one example of a method for forming a cell aggregate by using a container for forming a cell aggregate in the present invention. When an adherent cell C and a culture medium (not illustrated in the figure) are added into a container for forming a cell aggregate D, an adherent cell C adheres to a part of a container for forming a cell aggregate D (see FIG. 1A). It is considered that this is because an adherent cell C adheres to a region $D_1$ in which at least one of an amino group, a carboxyl group, and a hydroxyl group of a container for forming a cell aggregate D is present near a surface thereof. Then, when an adherent cell C is cultured, an adherent cell C proliferates and a cell aggregate C' of adherent cells C is formed autonomously (see FIG. 1B). It is considered that this is because a region $D_2$ in which an amino group, a carboxyl group, or a hydroxyl group of a container for forming a cell aggregate D is not present near a surface thereof inhibits adhesion of an adherent cell C, and accordingly, proliferated adherent cells C are formed on an adherent cell C. Thus, when an adherent cell C is cultured by using a container for forming a cell aggregate D, it is possible to form a cell aggregate C' of an adherent cell C.

A form of a container for forming a cell aggregate in the present invention is not particularly limited, and there is provided a dish, a multi-well plate, a flask, a roller bottle, a unit of a device having a cell culturing process, or the like.

A First Embodiment of a Container for Forming a Cell Aggregate in the Present Invention A first embodiment of a container for forming a cell aggregate in the present invention is manufactured by reacting a surface modifying agent having a functional group having a reactivity with a carboxyl group, an amino group, or a hydroxyl group, and a phosphorylcholine-like group, with a container in which a carboxyl group, an amino group, and a hydroxyl group are present near a surface thereof. Herein, a molecular weight of a surface modifying agent is 225-650. Thereby, it is possible to introduce a phosphorylcholine-like group at a high density.

A method for introducing an amino group near a surface of a container is not particularly limited, and there is provided a nitrogen plasma treatment, an ammonia plasma treatment, a method for reacting a surface treating agent, a silicone vapor phase treatment, or the like.

In a nitrogen plasma treatment, an amino group is introduced near a surface of a container by generating a low temperature plasma under a nitrogen gas atmosphere (for example, see Surface and Coatings Technology 116-119 (1999) 802-807, Colloids and Surfaces A: Physicochem. Eng. Aspects 195 (2001) 81-95, Macromol. Chem. Phys. 200. 989-996 (1999)). Specifically, after a container is put in a reactor and evacuation inside a reactor is conducted by a vacuum pump, nitrogen gas is introduced thereinto and glow discharge is conducted.

In an ammonia plasma treatment, an amino group is introduced near a surface of a container by generating a low temperature plasma under an ammonia gas atmosphere. Specifically, after a container is put in a reactor and evacuation inside a reactor is conducted by a vacuum pump, ammonia gas is introduced thereinto and glow discharge is conducted.

A material for making a container is not particularly limited and there is provided a polyvinyl chloride, an acryl resin, a polystyrene, a polypropylene, a polyethylene, a polyester, a cycloolefin resin, a polycarbonate, a glass, or the like.

In a method for reacting a surface treating agent, an amino group is introduced near a surface of a container in which at least one of a functional group capable of producing a silanol group through hydrolysis of an alkoxysilyl group or the like, a silanol group, a hydroxyl group originating from a semi-metal oxide, and a hydroxyl group originating from a metal oxide is present near a surface thereof, by using a surface treating agent such as an alkoxy silane, chlorosilane, or silazane having an amino group. Specifically, after a mixed liquid of water/2-propanol is first charged into a container and 3-aminopropyltrimethoxysilane is added thereto, heating at 100° C. is conducted to cause a reaction for 6 hours. Then, after cooling is conducted at room temperature, washing with methanol and drying are conducted.

A material for making a container is not particularly limited and there is provided a 3-trimethoxysilylpropyl methacrylate-methyl methacrylate-divinylbenzene copolymer, a polyvinyl chloride, an acryl resin, a polystyrene, a polypropylene, a polyethylene, a polyester, a cycloolefin resin, a polycarbonate, a silica, a glass, an alumina, a talc, a clay, a mica, an asbestos, a titanium oxide, a zinc flower, an iron oxide, or the like.

In a silicone vapor phase treatment, after a hydroxyl group is introduced near a surface of a container by using 1,3,5,7-tetramethylcyclotetrasiloxane, an amino group is introduced near a surface of a container by reacting an alkene having an amino group therewith (for example, see Japanese Examined Patent Application Publication No. 1-54379, Japanese Examined Patent Application Publication No. 1-54380, or Japanese Examined Patent Application Publication No. 1-54381). Specifically, 1,3,5,7-tetramethylcyclotetrasiloxane and a container are first put in a desiccator and degassing is conducted by an aspirator. Then, after a reaction is conducted at 80° C. for 16 hours, a container is removed therefrom and drying is conducted at 120° C. Furthermore, after an obtained container is dipped in ethanol and an allylamine is added thereto, a solution of chloroplatinic acid in ethanol is added thereto and agitation is conducted at 60° C. for 2 hours. After a reaction is completed, washing with ethanol and drying under a reduced pressure are conducted.

A material for making a container is not particularly limited, and there is provided a styrene-divinylbenzene copolymer, a polyvinyl chloride, an acryl resin, a polystyrene, a polypropylene, a polyethylene, a polyester, a cycloolefin resin, a polycarbonate, a mica, a talc, a kaolin, an alumina, a titanium oxide, a zinc oxide, an iron oxide, or the like.

An alkene having an amino group is not limited to allylamine, and it is possible to be an amine having a vinyl group, an amine having an acryl group, or the like. Furthermore, an amino group may be protected with a butoxycarbonyl group, a benzyloxycarbonyl group, or the like. Furthermore, for example, an alkene having a functional group capable of introducing an amino group through a reaction with a diamine, such as an epoxy group, may be used, instead of an alkene having an amino group.

A method for introducing a carboxyl group and/or a hydroxyl group near a surface of a container is not particularly limited, and there is provided an oxygen plasma treatment, an ozone treatment, a water vapor plasma treatment, or the like.

In an oxygen plasma treatment, a carboxyl group and a hydroxyl group are introduced near a surface of a container by generating a low temperature plasma under an oxygen gas atmosphere. Specifically, after a container is put in a reactor and evacuation inside a reactor is conducted by a vacuum pump, an oxygen gas is introduced thereinto and glow discharge is conducted.

In an oxygen treatment, a carboxyl group and a hydroxyl group are introduced near a surface of a container by charging an aqueous solution of ozone into a container. Specifically, an aqueous solution of ozone at 40 ppm is charged into a container and treatment is conducted at room temperature for 15 minutes.

In a water vapor plasma treatment, a hydroxyl group is introduced near a surface of a container by generating a low temperature plasma under a water vapor atmosphere. Specifically, after a container is put in a reactor and evacuation inside a reactor is conducted by a vacuum pump, a water vapor is introduced thereinto and glow discharge is conducted.

A material for making a container is not particularly limited, and there is provided a polystyrene, a polyethylene terephthalate, a polycarbonate, a polymethyl methacrylate, a polytetrafluoroethylene, a polyether ether ketone, a cycloolefin resin, a polycarbonate, or the like.

A method for introducing a carboxyl group near a surface of a container is not particularly limited, and there is provided a method for reacting a surface treating agent, a silicone vapor phase treatment, or the like.

In a method for reacting a surface treating agent, a carboxyl group is introduced near a surface of a container in which at least one of a functional group capable of producing a silanol group through hydrolysis of an alkoxysilyl group or the like, a silanol group, a hydroxyl group originating from a semimetal oxide, and a hydroxyl group originating from a metal oxide is present near a surface of a container, by using a surface treating agent such as an alkoxysilane, chlorosilane, or silazane having a carboxyl group. Specifically, triethoxysilylpropylsuccinic anhydride is first dissolved in N,N-dimethylformamide, then a distilled water and 4-dimethylaminopyridine are added thereinto, and agitation is conducted at room temperature for 16 hours, to synthesize a silane coupling agent having a carboxyl group. Then, after a mixed liquid of water/2-propanol is charged into a container and a silane coupling agent having a carboxyl group is added thereto, heating at 100° C. is conducted to cause a reaction for 6 hours. Furthermore, after cooling is conducted at room temperature, washing with methanol and drying are conducted.

A material for making a container is not particularly limited, and there is provided 3-trimethoxysilylpropyl methacrylate-methyl methacrylate-divinylbenzene copolymer, a silica, a glass, an alumina, a talc, a clay, a mica, an asbestos, a titanium oxide; a zinc flower, an iron oxide, or the like.

In a silicone vapor phase treatment, after a hydrosilyl group is introduced near a surface of a container by using 1,3,5,7-tetramethylcyclotetrasiloxane, a carboxyl group is introduced near a surface of a container by reacting an alkene having a carboxyl group therewith (for example, see Japanese Examined Patent Application Publication No. 1-54379, Japanese Examined Patent Application Publication No. 1-54380, or Japanese Examined Patent Application Publication No. 1-54381). Specifically, a container in which 1,3,5,7-tetramethylcyclotetrasiloxane is charged is first put in a desiccator and degassing is conducted by an aspirator. Then, after a reaction is conducted at 80° C. for 16 hours, a container is removed therefrom and drying at 120° C. is conducted. Furthermore, after an obtained container is dipped in ethanol and allylcarboxylic acid is added thereto, a solution of chloroplatinic acid in ethanol is added thereto and agitation is conducted at 60° C. for 2 hours. After a reaction is completed, washing with ethanol and drying under a reduced pressure are conducted.

A material for making a container is not particularly limited, and there is provided a styrene-divinylbenzene copolymer, a mica, a talc, a kaolin, an alumina, a titanium oxide, a zinc oxide, an iron oxide, or the like.

An alkene having a carboxyl group is not limited to allylcarboxylic acid, and it is possible to be a carboxylic acid having a vinyl group, a carboxylic acid having an acryl group, or the like.

A method for introducing an amino group, a carboxyl group, and a hydroxyl group near a surface of a container is not particularly limited, and there is provided a method for conducting a plasma treatment under an atmosphere including an oxygen gas and an ammonia gas or the like. Specifically, after a container is put in a reactor and evacuation inside a reactor is conducted by a vacuum pump, an oxygen gas and an ammonia gas are introduced thereinto and glow discharge is conducted to generate a low temperature plasma.

For a functional group having a reactivity with a carboxyl group, there is provided an amino group, a hydroxyl group, or the like, and an amino group is preferable because a reactivity thereof is high.

For a functional group having a reactivity with an amino group or a hydroxyl group, there is provided a carboxyl group, an aldehyde group, or the like, and a carboxyl group is preferable because a reactivity thereof is high.

Further more, for a surface modifying agent, it is preferable that a functional group having a reactivity with a carboxyl group, an amino group, or a hydroxyl group is bonded to a phosphorylcholine-like group via a spacer. A spacer is not particularly limited, and there is provided a methylene group, an oxyethylene group, an alkylene group having one or more amino groups, or the like.

Next, a surface modifying agent having an amino group and a phosphorylcholine-like group will be described.

A surface modifying agent having an amino group and a phosphorylcholine-like group is not particularly limited, and there is provided a compound disclosed in Japanese Patent Application Publication No. 2006-007203, Japanese Patent Application Publication No. 2006-007204, or Japanese Patent Application Publication No. 2008-174491, or the like.

When a carboxyl group which is present near a surface of a container and an amino group possessed by a surface modifying agent are condensed through a general reaction, an amide linkage is formed. Specifically, after a solution of N-hydroxysuccinimide and/or 1-ethyl-3-(3-dimethylaminopropyl)carbodiimide is charged into a container to active-esterify a carboxyl group of a container, a surface modifying agent is added thereto.

Next, a surface modifying agent having a hydroxyl group and a phosphorylcholine-like group will be described.

A surface modifying agent having a hydroxyl group and a phosphorylcholine-like group is not particularly limited, and there is provided L-α-glycerophosphorylcholine, or the like.

When a carboxyl group which is present near a surface of a container and a hydroxyl group possessed by a surface modifying agent are condensed through a general reaction, an ester linkage is formed. Specifically, after a hydroxyl group of a surface modifying agent is activated by using cyanogen bromide, charging thereof into a container is conducted.

Next, a surface modifying agent having a carboxyl group and a phosphorylcholine-like group will be described.

A surface modifying agent having a carboxyl group and a phosphorylcholine-like group is not particularly limited, and there is provided a compound disclosed in Japanese Patent Application Publication No. 2006-011381 or the like.

When an amino group which is present near a surface of a container and a carboxyl group possessed by a surface modifying agent are condensed through a general reaction, an amide linkage is formed. Specifically, after a surface modifying agent is added into a solution of N-hydroxysuccinimide and/or 1-ethyl-3-(3-dimethylaminopropyl)carbodiimide to active-esterify a carboxyl group, charging thereof into a container is conducted.

When a hydroxyl group which is present near a surface of a container and a carboxyl group possessed by a surface modifying agent are condensed through a general reaction, an ester linkage is formed. Specifically, after a hydroxyl group of a surface modifying agent is activated by using cyanogen bromide, a container is dipped.

Next, a surface modifying agent having an aldehyde group and a phosphorylcholine-like group will be described.

A surface modifying agent having an aldehyde group and a phosphorylcholine-like group is not particularly limited, and there is provided a compound disclosed in Japanese Patent Application Publication No. 2006-011383 or the like.

When an amino group which is present near a surface of a container and an aldehyde group possessed by a surface modifying agent are condensed through a general reaction, an imino linkage is formed. Specifically, after a surface modifying agent and methanol are charged into a container and leaving thereof at room temperature for 6 hours is conducted, sodium cyanotrihydroborate is added thereto at 0° C. and heating and agitation thereof are conducted overnight. In addition, it is also possible to use a protic solvent such as water, ethanol, or 2-propanol, other than methanol, for a reaction solvent, and an introduction rate in a case where methanol is used tends to be high.

When a hydroxyl group which is present near a surface of a container and an aldehyde group possessed by a surface modifying agent are added through a general reaction, an acetal linkage is formed. Specifically, after a container and a surface modifying agent are left in methanol at room temperature for 6 hours, sodium cyanotrihydroborate is added thereto at 0° C. and heating and agitation thereof are conducted overnight. In addition, it is also possible to use a protic solvent such as water, ethanol, or 2-propanol, other than methanol, for a reaction solvent, and an introduction rate in a case where methanol is used tends to be high.

Additionally, a surface modifying agent having a functional group having a reactivity with an aldehyde group and a phosphorylcholine-like group may be reacted by using a container in which an aldehyde group and an amino group and/or a hydroxyl group are present near a surface thereof, instead of a container in which a carboxyl group, an amino group, and a hydroxyl group are present near a surface thereof.

A method for introducing an aldehyde group near a surface of a container is not particularly limited, and there is provided a method for reacting glutaraldehyde with a container in which an amino group is present near a surface thereof, or the like.

For a functional group having a reactivity with an aldehyde group, there is provided an amino group, a hydroxyl group, or the like, and an amino group is preferable because a reactivity thereof is high.

Furthermore, for a surface modifying agent, it is preferable that a functional group having a reactivity with an aldehyde group is bonded to a phosphorylcholine-like group via a spacer. A spacer is not particularly limited, and there is provided a methylene group, an oxyethylene group, an alkylene group having one or more amino groups, or the like.

Next, a surface modifying agent having an amino group and a phosphorylcholine-like group will be described.

A surface modifying agent having an amino group and a phosphorylcholine-like group is not particularly limited, and there is provided a compound disclosed in Japanese Patent Application Publication No. 2006-007203, Japanese Patent Application Publication No. 2006-007204, or Japanese Patent Application Publication No. 2008-174491, or the like.

When an aldehyde group which is present near a surface of a container and an amino group possessed by a surface modifying agent are condensed through a general reaction, an imino linkage is formed. Specifically, after a container and a surface modifying agent are left in ethanol at room temperature for 6 hours, sodium cyanotrihydroborate is added thereto at 0° C. and heating and agitation thereof is conducted overnight. In addition, it is also possible to use a protic solvent such as water, ethanol, or 2-propanol, other than methanol, for a reaction solvent, and an introduction rate in a case where methanol is used tends to be high.

Next, a surface modifying agent having a hydroxyl group and a phosphorylcholine-like group will be described.

A surface modifying agent having a hydroxyl group and a phosphorylcholine-like group is not particularly limited, and there is provided L-α-glycerophosphorylcholine, or the like.

When an aldehyde group which is present near a surface of a container and a hydroxyl group possessed by a surface modifying agent are added through a general reaction, an acetal linkage is formed. Specifically, after a container and a surface modifying agent are left in methanol at room temperature for 6 hours, sodium cyanotrihydroborate is added thereto at 0° C. and heating and agitation thereof is conducted overnight. In addition, it is also possible to use a protic solvent such as water, ethanol, or 2-propanol, other than methanol, for a reaction solvent, and an introduction rate in a case where methanol is used tends to be high.

Furthermore, a surface modifying agent having a functional group having a reactivity with an amino group or a hydroxyl group and a phosphorylcholine-like group may be reacted by using a container in which a carboxyl group, an amino group, or a hydroxyl group is present near a surface thereof, instead of a container in which a carboxyl group, an amino group, and a hydroxyl group are present near a surface thereof.

Moreover, a surface modifying agent having a functional group having a reactivity with an amino group or a hydroxyl group and a phosphorylcholine-like group may be reacted by using a container in which an amino group and a hydroxyl group are present near a surface thereof, instead of a container in which a carboxyl group, an amino group, and a hydroxyl group are present near a surface thereof, so that an unreacted amino group and/or hydroxyl group remain(s) near a surface of a container.

Furthermore, a surface modifying agent having a functional group having a reactivity with a carboxyl group, an amino group, or a hydroxyl group and a phosphorylcholine-like group may be reacted by using a container in which a carboxyl group, an amino group, or a hydroxyl group is present near a surface thereof, instead of a container in which a carboxyl group, an amino group, and a hydroxyl group are present near a surface thereof, so that an unreacted carboxyl group, amino group, or hydroxyl group remains near a surface of a container.

A Second Embodiment of a Container for Forming a Cell Aggregate in the Present Invention A second embodiment of a container for forming a cell aggregate in the present invention is manufactured by reacting a first surface modifying agent having a functional group capable of producing a silanol group through hydrolysis thereof and a phosphorylcholine-like group and a second surface modifying agent having a functional group capable of producing a silanol group through hydrolysis thereof and at least one of an amino group, a carboxyl group, and a hydroxyl group, with a container in which at least one of a functional group capable of producing a silanol group through hydrolysis thereof, a silanol group, a hydroxyl group originating from a semimetal oxide, and a hydroxyl group originating from a metal oxide is present near a surface thereof. Herein, a molecular weight of a first surface modifying agent is 315-650. Thereby, it is possible to introduce a phosphorylcholine-like group at a high density.

For a method for introducing a functional group capable of producing a silanol group through hydrolysis thereof and/or a silanol group near a surface of a container, there is provided a method for applying an application liquid containing a polymer having a functional group capable of producing a silanol group through hydrolysis thereof (referred to as a hydrolysable polymer, below) and an alkoxysilane to a container.

When an application liquid containing a hydrolysable polymer and an alkoxysilane is applied to a container, a hydrolysable polymer and an alkoxysilabe are hydrolyzed to produce a silanol group. Furthermore, a hydrolysable polymer is cross-linked through dehydration and condensation of silanol groups thereof with one another to form a layer of a cross-linked polymer in which a silanol group is introduced. Specifically, after an application liquid is applied to a material, water, an acid, or an alkali is applied thereto and/or heating is conducted. Furthermore, after water, an acid, or an alkali is applied to a material, an application liquid may be applied thereto. Moreover, water, an acid, or an alkali may be mixed into an application liquid. In such a case, it is preferable to prepare an application liquid at the time of application appropriately, because hydrolysis thereof is caused in an application liquid. In addition, when water, an acid, or an alkali is used, heating may be conducted, but, generally, a reaction sufficiently proceeds at room temperature. Furthermore, even if water, an acid, or an alkali is not used, a reaction gradually proceeds due to atmospheric moisture.

An acid or alkali to be used for hydrolysis is not particularly limited as long as it is possible to conduct hydrolysis, wherein it is possible to mix and use two or more kinds thereof and use thereof in an aqueous solution may be conducted.

For an application liquid, it is possible to use a hydrolysable polymer and an alkoxysilane which are dissolved or dispersed in an organic solvent. An organic solvent is not particularly limited, and there is provided an aliphatic hydrocarbon, an aromatic hydrocarbon, a chlorinated hydrocarbon, an ether, an alcohol such as a 1-4-hydric aliphatic alcohol with a carbon number of 1-4, a cellosolve such as ethylcellosolve or butylcellosolve, a dioxane, methyl acetate, a diformamide, or the like, wherein two or more kinds thereof may be used in combination.

A content of a hydrolysable polymer in an application liquid is generally 0.001-20% by mass and 0.1-5% by mass is preferable. If a content of a hydrolysable polymer in application liquid is less than 0.001% by mass, a sufficient effect may not be obtained in a single application, and if it is more than 20% by mass, an application property may be degraded.

Furthermore, a mass ratio of a hydrolysable polymer to an alkoxysilane is generally 0.01-20%, and 0.2-5% is preferable. If a mass ratio of a hydrolysable polymer to an alkoxysilane is less than 0.01%, a strength of a cross-linked polymer layer may be insufficient, and if it is more than 20%, an amount of a silanol group to be introduced into a cross-linked polymer layer may be insufficient.

A method for applying an application liquid is not particularly limited, and there is provided a dip coating method, a spray coating method, a spin-cast method, or the like.

A material for making a container is not particularly limited and there is provided an organic material such as a PP (polypropylene), a cycloolefin resin, a polycarbonate, a PET (polyethylene terephthalate), a PEEK, a fluororesin, a polystyrene, or a polyvinyl chloride; an inorganic material such as gold, titanium, aluminum, iron, copper, a stainless steel, an alumina, a titanium oxide, or a zinc oxide; or the like.

A hydrolysable polymer is not particularly limited as long as a polymer has a functional group capable of producing a silanol group through hydrolysis thereof, and it is possible to use a homopolymer or copolymer (as referred to as a polymer (A), below) obtained by polymerizing a monomer (A-1) represented by a general formula of:

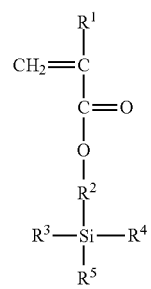

(in the formula, $R^1$ is a hydrogen atom or a methyl group, $R^2$ is an alkylene group with a carbon number of 1-6, and preferably a propylene group, and each of $R^3$, $R^4$, and $R^5$ is independently an alkoxyl group with a carbon number of 1-6, and preferably a methoxyl group or an ethoxyl group.). Herein, two or more kinds of monomers (A-1) may be used.

Furthermore, when a polymer (A) is synthesized, a monomer (A-2) represented by a general formula of:

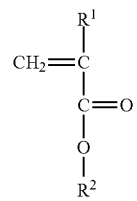

(in the formula, $R^1$ is a hydrogen atom or a methyl group, and $R^2$ is a linear, branched, or cyclic alkyl group with a carbon number of 1-18, preferably an alkyl group with a carbon number of 1-6, and particularly preferably a methyl group.) may be copolymerized. Herein, two or more kinds of monomers (A-2) may be used.

Furthermore, when a polymer (A) is synthesized, a monomer (A-3) represented by a general formula of:

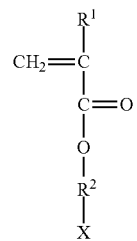

(in the formula, $R^1$ is a hydrogen atom or a methyl group, $R^2$ is an alkylene group with a carbon number of 1-6 and preferably an ethylene group, a propylene group, or 2-hydroxypropylene group, and X is a functional group (X-1) represented by a general formula of:

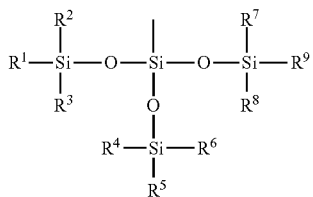

(in the formula, each of $R^1$, $R^2$, $R^3$, $R^4$, $R^5$, $R^6$, $R^7$, and $R^8$ is independently a linear or branched alkyl group with a carbon number of 1-6 and preferably a methyl group.), a functional group (X-2) represented by a general formula of:

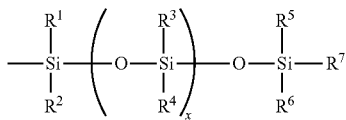

(in the formula, each of $R^1$, $R^2$, $R^3$, $R^4$, $R^5$, and $R^6$ is independently a linear or branched alkyl group with a carbon number of 1-6 and preferably a methyl group, $R^7$ is a linear or branched alkyl group with a carbon number of 1-6 and preferably a butyl group, and x is a positive integer.), or a functional group (X-3) represented by a general formula of:

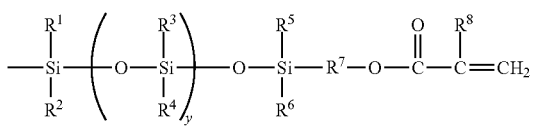

(in the formula, each of $R^1$, $R^2$, $R^3$, $R^4$, $R^5$, and $R^6$ is independently a linear or branched alkyl group with a carbon number of 1-6 and preferably a methyl group, $R^7$ is an alkylene group with a carbon number of 1-6 and preferably an ethylene group, a propylene group, or a 2-hydroxypropylene group, $R^8$ is a hydrogen atom or a methyl group, and y is a positive integer.)) may be copolymerized. In addition, when X is a functional group (X-2) or (X-3), it is preferable that a molecular weight of a monomer (A-3) is 1000-100000 and 2000-20000 is particularly preferable. Herein, two or more kinds of monomers (A-3) may be used.

Furthermore, when a polymer (A) is synthesized, a monomer (A-4) represented by a general formula of:

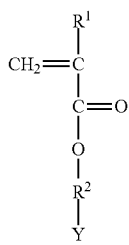

(in the formula, $R^1$ is a hydrogen atom or a methyl group, $R^2$ is an alkylene group with a carbon number of 1-6 and preferably an ethylene group or a propylene group, and Y is a functional group (Y-1) represented by a general formula of:

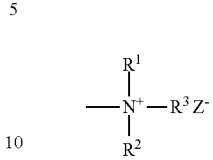

(in the formula, each of $R^1$, $R^2$, and $R^3$ is independently an alkyl group with a carbon number of 1-6 and preferably a methyl group, and $Z^-$ is a halide ion or a conjugate ion of an organic acid or inorganic acid.) or a functional group (Y-2) represented by a general formula of:

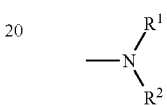

(in the formula, each of $R^1$ and $R^2$ is independently an alkyl group with a carbon number of 1-6 and preferably a methyl group.)) may be copolymerized. Herein, two or more kinds of monomers (A-4) may be used.

That is, when a polymer (A) is polymerized, at least one of a monomer (A-2), a monomer (A-3), and a monomer (A-4) may be copolymerized with a monomer (A-1).

It is preferable that a content of a monomer (A-1) in all of monomers to be used to synthesize a polymer (A) is 40-85% by mass. If a content of a monomer (A-1) in all of monomers is less than 40% by mass, a crosslink density may be lowered, whereby an effect of providing a hydrophilicity may not sufficiently be maintained, and if it is more than 85% by mass, a uniformity of a cross-linked polymer layer may be lowered.

Furthermore, a content of a monomer (A-2) in all of monomers to be used to synthesize a polymer (A) is generally 1-75% by mass, and 10-60% by mass is preferable. If a content of a monomer (A-2) in all of monomers is less than 1% by mass, a water resisting property of a cross-linked polymer layer may be degraded, and if it is more than 75% by mass, a polymer (A) may be difficult to dissolve in an alcohol.

Moreover, a content of a monomer (A-3) in all of monomers to be used to synthesize a polymer (A) is generally 1-70% by mass, and 5-60% by mass is preferable. If a content of a monomer (A-3) in all of monomers is less than 1% by mass, a water resisting property of a cross-linked polymer layer may be degraded, and if it is more than 70% by mass, a polymer (A) may be difficult to dissolve in an alcohol.

Furthermore, a ratio of a mass of a monomer (A-4) to a total mass of a monomer (A-1), monomer (A-2), and monomer (A-3) is generally 0.01-1, and 0.05-0.5 is preferable. If this ratio is less than 0.01, a flexibility of a cross-linked polymer layer may be degraded, and if it is more than 1, a water resisting property of a cross-linked polymer layer may be degraded.

It is preferable that a number-average molecular weight of a polymer (A) is 2000-150000. If a number average molecular weight of a polymer (A) is less than 2000, a period of time for forming a cross-linked polymer layer may be long, and if it is more than 150000, a viscosity of an application liquid may be high, whereby an application property or workability may be degraded.

In addition, a specific example and manufacturing method for a polymer (A) are disclosed in Japanese Patent Application Publication No. 11-302129 or the like.

Furthermore, for a hydrolysable polymer, it is possible to use a homopolymer or copolymer (referred to as a polymer (B), below) having a structural unit (B-1) represented by a general formula of:

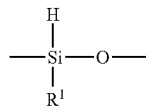

(in the formula, $R^1$ is an alkyl group with a carbon number of 1-22 or a phenyl group, and preferably a methyl group.). Herein, a polymer (B) may have two or more kinds of structural units (B-1).

Furthermore, a polymer (B) may have a structural unit (B-2) represented by a general formula of:

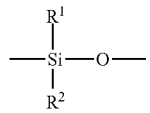

(in the formula, each of $R^1$ and $R^2$ is independently an alkyl group with a carbon number of 1-22 or a phenyl group, and preferably a methyl group.). Herein, a polymer (B) may have two or more kinds of structural units (B-2).

It is preferable that a content of a structural unit (B-1) in a polymer (B) is 1-90% by mass. If a content of a structural unit (B-1) is less than 1% by mass, a crosslink density may be lowered, whereby an effect of providing a hydrophilicity may not sufficiently be maintained, and if it is more than 90% by mass, a uniformity of a cross-linked polymer layer may be degraded.

Moreover, it is preferable that a content of a structural unit (B-2) in a polymer (B) is 10-99% by mass. If a content of a structural unit (B-2) is less than 10% by mass, a uniformity of a cross-linked polymer layer may be degraded, and if it is more than 99% by mass, a crosslink density may be lowered, whereby an effect of providing a hydrophilicity may not sufficiently be maintained.

It is preferable that a number average molecular weight of a polymer (B) is 2000-500000. If a number average molecular weight is less than 2000, a period of time for forming a cross-linked polymer layer may be long, and if it is more than 500000, a viscosity of an application liquid may be high, whereby an application property or workability may be degraded.

For a hydrolysable polymer, a polymer (A) and a polymer (B) may be used in combination, and a hydrolysable polymer and a non-hydrolysable polymer may be used in combination. A non-hydrolysable polymer is not particularly limited, and there is provided a polymer (A) or polymer (B) having no functional group capable of producing a silanol group through hydrolysis thereof, or the like.

A method for introducing a silanol group near a surface of a container is not particularly limited, and there is provided a method for applying an application liquid containing a silicone resin to a container to form a film containing a silicone resin having a silanol group, or the like.

It is preferable that a contact angle of water on a film containing a silicone resin having a silanol group is 3-8°. It is difficult to form a film with a contact angle of water which is less than 3°, and if a film with a contact angle of water which is more than 8° is formed, it may not be possible to introduce a phosphorylcholine-like group at a high density.

A silicone resin contained in an application liquid is not particularly limited, and there is provided a resin obtained by hydrolyzing and subsequently condensing an alkoxysilane represented by a general formula of:

$(R^1O)_n Si(R^2)_{4-n}$ (in the formula, each of $R^1$ and $R^2$ is independently an alkyl group with a carbon number of 1-8 and n is an integer of 1-4, wherein a plurality of $R^2$ may be identical or different in a case where n is 1 or 2 and a plurality of $R^1$ may be identical or different in a case where n is 2 or 3.), wherein two or more kinds thereof may be used in combination. Herein, a silicone resin having a silanol group which is contained in a film with a contact angle of water being 3-8° may be identical to or may be different from a silicone resin contained in an application liquid.

An organic solvent contained in application liquid is not particularly limited, and there is provided an aliphatic hydrocarbon, an aromatic hydrocarbon, a chlorinated hydrocarbon, an ether, an alcohol such as a 1-4-hydric aliphatic alcohol with a carbon number of 1-4, a cellosolve such as ethylcellosolve or butylcellosolve, a dioxane, methyl acetate, a diformamide, or the like, wherein two or more kinds thereof may be used in combination.

A content of a silicone resin in an application liquid is generally 0.01-1% by mass and 0.1-1% by mass is preferable. If a content of a silicone resin in an application liquid is less than 0.001% by mass, a uniform film may not be formed, and if it is more than 20% by mass, an application property may be degraded.

A method for applying an application liquid is not particularly limited, and there is provided a dip coating method, a spray coating method, a spin-cast method, or the like.

A material for making a container is not particularly limited, and there is provided an organic material such as a polycarbonate, a PET (polyethylene terephthalate), a polystyrene, or an acryl resin; an inorganic material such as gold, titanium, aluminum, iron, copper, a stainless steel, an alumina, a titanium oxide, or a zinc oxide; or the like.

Furthermore, a container made of a glass may be used for a container in which a silanol group is present near a surface thereof.

A metal oxide for making a container in which a hydroxyl group originating from a metal oxide is present near a surface thereof is not particularly limited, and there is provided a titanium oxide, a zinc oxide, an iron oxide, a chromium oxide, an aluminum oxide, or the like.

A metal oxide for making a container in which a hydroxyl group originating from a semimetal oxide is present near a surface thereof is not particularly limited, and there is provided a germanium oxide, an arsenic oxide, a boron oxide, or the like.

For a functional group having a reactivity with at least one of a functional group capable of producing a silanol group through hydrolysis thereof, a silanol group, a hydroxyl group originating from a semimetal oxide, and a hydroxyl group originating from a metal oxide, there is provided a functional group capable of producing a silanol group through hydrolysis thereof.

Furthermore, it is preferable that a functional group capable of producing a silanol group through hydrolysis thereof is bonded to a phosphorylcholine-like group via a spacer in a first surface modifying agent. A spacer is not particularly limited, and there is provided a methylene group, an oxyethylene group, an alkylene group having one or more amino groups, or the like.

For a functional group capable of producing a silanol group through hydrolysis thereof, there is provided a hydrosilyl group, an alkoxysilyl group, a halosilyl group, an acyloxysilyl group, an aminosilyl group, or the like, wherein an alkoxysilyl group with a carbon number of 1-6 or a hydrosilyl group is preferable from the viewpoint of a stability, a reactivity, or the like.

A first surface modifying agent is not particularly limited as long as a functional group capable of producing a silanol group through hydrolysis thereof and a phosphorylcholine-like group are possessed, and there is provided a compound disclosed in Japanese Patent Application Publication No. 2006-011380.

A second surface modifying agent is not particularly limited as long as a functional group capable of producing a silanol group through hydrolysis thereof and at least one of an amino group, a functional group capable of producing a carboxyl group through hydrolysis thereof, and a functional group capable of producing a hydroxyl group through hydrolysis thereof are possessed, and there is provided a compound having an amino group such as 3-aminopropyltrimethoxysilane or p-aminophenyltrimethoxysilane; a compound having a functional group capable of producing a carboxyl group through hydrolysis thereof such as 3-(triethoxysilyl)propylsuccinic anhydride; a compound having a functional group capable of producing a hydroxyl group through hydrolysis thereof such as 3-glycidoxypropyltrimethoxysilane or 3-glycidoxypropylmethyldiethoxysilane; or the like, wherein two or more kinds thereof may be used in combination.

When a second surface modifying agent has a functional group capable of producing a carboxyl group and/or a hydroxyl group through hydrolysis thereof, it is possible to introduce a functional group capable of producing a carboxyl group and/or a hydroxyl group through hydrolysis thereof near a surface of a container and subsequently conduct hydrolysis thereof.

In addition, an amino group possessed by a second surface modifying agent may be protected by a protecting group. Furthermore, a second surface modifying agent may have a carboxyl group or hydroxyl group protected by a protecting group capable of conducting deprotection through a reaction other than hydrolysis thereof, instead of a functional group capable of producing a carboxyl group or hydroxyl group through hydrolysis thereof.

When a second surface modifying agent has at least one of an amino group, carboxyl group, and hydroxyl group protected by a protecting group, it is possible to introduce at least one of an amino group, carboxyl group, and hydroxyl group protected by a protecting group near a surface of a container and subsequently conduct deprotection thereof.

Next, a method for introducing a phosphorylcholine-like group and at least one of an amino group, a functional group capable of producing a carboxyl group through hydrolysis thereof, and a functional group capable of producing a hydroxyl group through hydrolysis thereof into a container in which at least one of a functional group capable of producing a silanol group through hydrolysis thereof, a silanol group, a hydroxyl group originating from a semimetal oxide, and a hydroxyl group originating from a metal oxide are present near a surface thereof will be described.

First, an application liquid containing a first surface modifying agent and a second surface modifying agent is applied to a container in which a functional group capable of producing a silanol group through hydrolysis thereof, a silanol group, a hydroxyl group originating from a semimetal oxide, and a hydroxyl group originating from a metal oxide are present near a surface thereof. Herein, a functional group capable of producing a silanol group through hydrolysis thereof is hydrolyzed to produce a silanol group. Furthermore, a surface of a container is modified through dehydration and condensation of at least one of a silanol group originating from a surface modifying agent, a silanol group originating from a container, a hydroxyl group originating from a semimetal oxide, and a hydroxyl group originating from a metal oxide. Specifically, after an application liquid is applied to a container, water, an acid, or an alkali may be applied thereto or heating thereof may be conducted. Furthermore, after water, an acid, or an alkali is applied to a container, an application liquid may be applied thereto. Moreover, water, an acid, or an alkali may be mixed into an application liquid. In this case, it is preferable to prepare an application liquid at the time of application appropriately, because hydrolysis is caused in an application liquid. In addition, when water, an acid, or an alkali is used, heating may be conducted, but, generally, a reaction sufficiently proceeds at room temperature. Furthermore, even if water, an acid, or an alkali is not used, a reaction gradually proceeds due to atmospheric moisture.

An acid or alkali is not particularly limited as long as it is possible to hydrolyze a functional group capable of producing a silanol group through hydrolysis thereof, wherein two or more kinds thereof may be used in combination. Additionally, an acid or alkali to be used for hydrolysis may be used in an aqueous solution.

It is possible to use an application liquid in which a first surface modifying agent and a second surface modifying agent are dissolved or dispersed in an organic solvent. For an organic solvent, there is provided an aliphatic hydrocarbon, an aromatic hydrocarbon, a chlorinated hydrocarbon, an ether, an alcohol such as a 1-4-hydric aliphatic alcohol with a carbon number of 1-4, a cellosolve such as ethylcellosolve or butylcellosolve, a dioxane, methyl acetate, a diformamide, or the like.

A content of a first surface modifying agent in an application liquid is generally 0.1-30% by mass, and 1-10% by mass is preferable. If a content of a first surface modifying agent in an application liquid is less than 0.1% by mass, it may not be possible to apply a first surface modifying agent sufficiently in a single application, and if it is more than 30% by mass, an application property may be degraded.

If a second surface modifying agent has an amino group, a ratio of an equivalent weight of a phosphorylcholine-like group of a first surface modifying agent to that of an amino group of a second surface modifying agent in an application liquid is generally 3/7-19.

A method for applying an application liquid is not particularly limited, and there is provided a dip coating method, a spray coating method, a spin-cast method, or the like.

In addition, each of an application liquid containing a first surface modifying agent and an application liquid containing a second surface modifying agent may be applied to a container.

Furthermore, a silanol group originating from a surface modifying agent and at least one of a silanol group originating from a container, a hydroxyl group originating from a semimetal oxide, and a hydroxyl group originating from a metal oxide may be reacted in such a manner that at least one of an unreacted silanol group, a hydroxyl group originating from a semimetal oxide, and a hydroxyl group originating from a metal oxide remains near a surface of a container.

A Third Embodiment of a Container for Forming a Cell Aggregate in the Present Invention In a third embodiment of a container for forming a cell aggregate in the present invention, a layer containing a resin having a phosphorylcholine-like group and at least one of an amino group, a carboxyl group, and a hydroxyl group is famed on a surface thereof.

A resin having a phosphorylcholine-like group and at least one of an amino group, a carboxyl group, and a hydroxyl group is not particularly limited, and there is provided a resin obtained by copolymerizing a monomer having a phosphorylcholine-like group and at least one of a monomer having an amino group, a monomer having a carboxyl group, and a monomer having a hydroxyl group (for example, see Japanese Patent Application Publication No. 7-184990).

A material for making a container is not particularly limited, and there is provided an organic material such as a cycloolefin resin, a polycarbonate, a PET (polyethylene terephthalate), a polystyrene, or an acryl resin; an inorganic material such as gold, titanium, aluminum, iron, copper, a stainless steel, an alumina, a titanium oxide, or a zinc oxide; or the like.

In addition, when a container made of an organic material is used, it is preferable to use a resin obtained by copolymerizing a monomer having a phosphorylcholine-like group, a monomer having at least one of an amino group, a carboxyl group, and a hydroxyl group, and a monomer having a hydrophobic group in view of an adhesive property thereof to a container.

A monomer having a hydrophobic group is not particularly limited, and there is provided butyl methacrylate or the like.

For a method for forming a layer containing a resin having a phosphorylcholine-like group and at least one of an amino group, a carboxyl group, and a hydroxyl group near a surface of a container, there is provided a method for applying an application liquid containing a resin having a phosphorylcholine-like group and at least one of an amino group, a carboxyl group, and a hydroxyl group to a container.

It is possible to use an application liquid in which a resin is dissolved or dispersed in an organic solvent. For an organic solvent, there is provided an aliphatic hydrocarbon, an aromatic hydrocarbon, a chlorinated hydrocarbon, an ether, an alcohol such as a 1-4^hydric aliphatic alcohol with a carbon number of 1-4, a cellosolve such as ethylcellosolve or butylcellosolve, a dioxane, methyl methacrylate, a diformamide, or the like.

A content of a resin in an application liquid is generally 0.1-30% by mass, and 1-10% by mass is preferable. If a content of a resin in an application liquid is less than 0.1% by mass, it may not be possible to apply a resin sufficiently in a single application, and if it is more than 30% by mass, an application property may be degraded.

A method for applying an application liquid is not particularly limited, and there is provided a dip coating method, a spray coating method, a spin-cast method, or the like.

In a method for forming a cell aggregate in the present invention, a somatic cell is cultured by using a container for forming a cell aggregate in the present invention to form a cell aggregate. Thereby, it is possible to form a cell aggregate of adherent cells. In the specification and claims for the present application, a somatic cell includes a pluripotent stem cell.

In addition, when a non-adherent cell capable of forming a cell aggregate through suspension culture is suspension-cultured by using a method for forming a cell aggregate in the present invention, it is possible to form a cell aggregate.

A somatic cell capable of being applied to a method for forming a cell aggregate in the present invention is not particularly limited, and there is provided an adherent cell such as a mesenchymal stem cell, a hepatic cell, a hepatic stem cell, a cardiac muscle cell, a cancer cell, a cancer stem cell, a fibroblast, a nerve cell, or a vascular endothelial precursor cell; or a non-adherent cell such as a neural stem cell, a hematopoietic stem cell, or a lymphoma cell.

When a somatic cell originating from a mammal such as a human being, a rat, a mouse, or primate is applied to a method for forming a cell aggregate in the present invention, usefulness is provided to a below-mentioned method for screening a substance or method for exploring a cell function.

In the present invention, a method for culturing a somatic cell is not particularly limited, and it is possible to apply a publicly-known condition depending on a somatic cell, wherein there is provided a method for culturing a somatic cell at 37° C. under an atmosphere containing 5% by volume of carbon dioxide by using a Dulbecco's modified culture medium (DMEM) containing 10% by mass of a fetal bovine serum (FBS), 1 mM of glutamine, and a suitable amount of an antibiotic substance or the like.

In a method for screening a substance in the present invention, a substance is screened by using a cell aggregate formed by a method for forming a cell aggregate in the present invention. Herein, it is possible to apply a method for screening a substance in the present invention to a publicly-known method for screening a substance such as a method for evaluating a toxicity of a substance by using a hepatic cell or a cardiac muscle cell or a method for testing an effect of a drug by using a cancer cell. For a method for evaluating a toxicity of a substance, there is provided a method based on cell proliferation such as a MTT assay or an Alamar Blue assay. Furthermore, it is also possible to quantify a quantity of SDF-1, LIF, EGFR, or the like which is a factor associated with yielding or release of an inflammatory cytokine or canceration by a method such as RT-PCR or ELISA.

Furthermore, it is possible to screen a substance by using a cell aggregate of somatic cells for each individual, so that a method for screening a substance in the present invention is applied to a tailor-made medicine.

In a method for exploring a cell function in the present invention, a cell function is explored by using a cell aggregate formed by a method for forming a cell aggregate in the present invention. Herein, it is possible to apply a method for exploring a cell function in the present invention to a publicly-known method for exploring a cell function such as a method for elucidating a biochemical function of a somatic cell or a method for exploring a biomarker.

Practical Example 1

After 1 g of N-hydroxysuccinimide and a 1% by mass aqueous solution of 1 g of 1-ethyl-3-(3-dimethylaminopropyl)carbodiimide were charged into a Primaria dish (produced by Nippon Becton Dickinson Co., Ltd.), a solution in which 1 g of a compound represented by a chemical formula of:

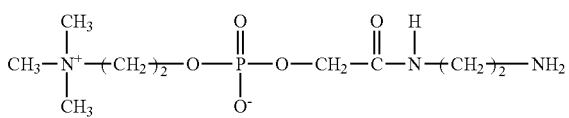

was dissolved in 100 ml of water was added thereto, to conduct esterification. Then, after a liquid was removed from the Primaria dish and dried at room temperature for 5 hours, washing with water and drying were conducted to obtain a container for forming a cell aggregate. Herein, the Primaria dish is a dish made of a polystyrene and subjected to plasma treatment under an atmosphere containing oxygen and ammonia.

Figure 2A:
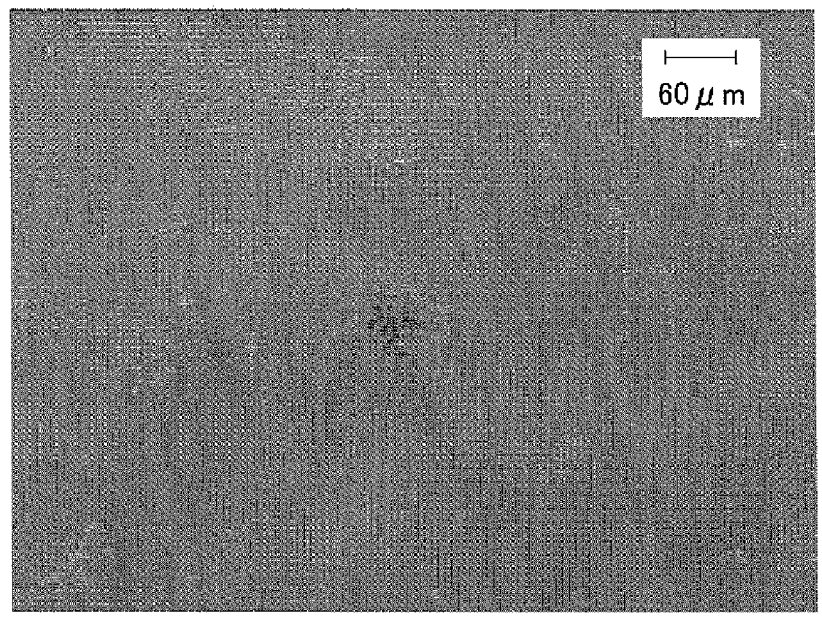
FIG. 2A is an optical micrograph illustrating a cell aggregate in practical example 1 (in a case of culturing for 2 days).
Figure 2B:
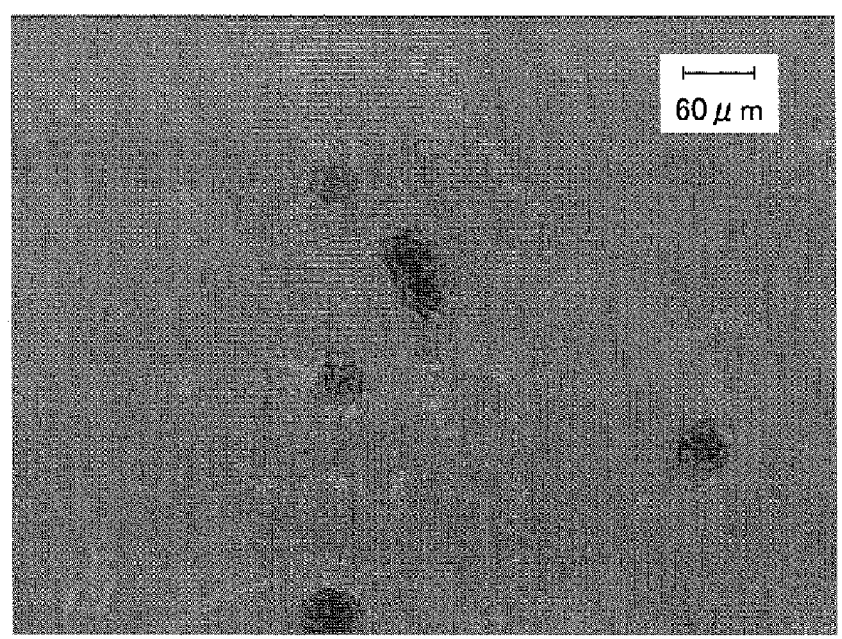
FIG. 2B is an optical micrograph illustrating a cell aggregate in practical example 1 (in a case of culturing for 5 days).

When 10 ml of a MensenPRO RS culture medium produced by Invitrogen Corporation) and 1×10⁶/dish of stem cells originating from a human fat (produced by Invitrogen Corporation) as mesenchymal cells were added into the container for forming a cell aggregate to culture the stem cells originating from a human fat, the cells proliferated and formed a cell aggregate (see FIG. 2A and FIG. 2B).

Comparative Example 1

Figure 3:
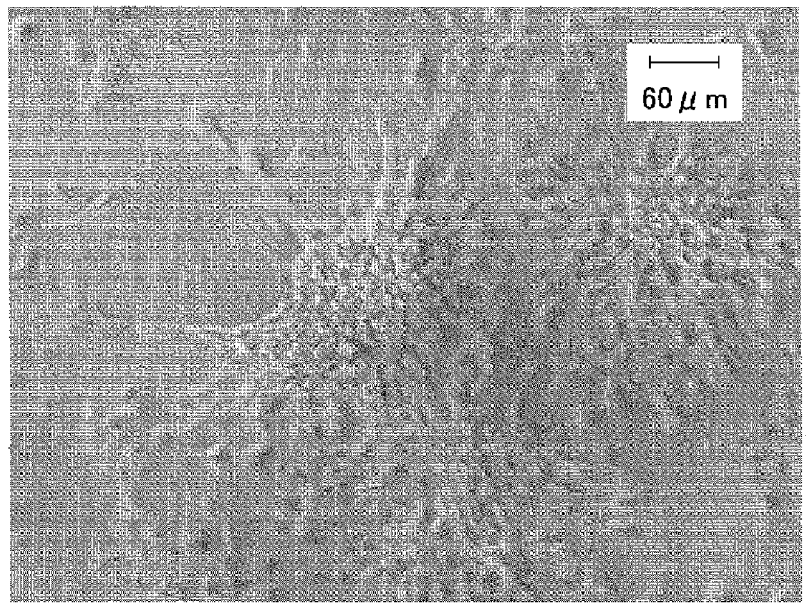
FIG. 3 is an optical micrograph illustrating a cultured cell in comparative example 1 (in a case of culturing for 5 days).

When 10 ml of a MensenPRO RS culture medium produced by Invitrogen Corporation) and 1×10⁶/dish of stem cells originating from a human fat (produced by Invitrogen Corporation) were added into a petri dish made of a polystyrene and subjected to no surface treatment (produced by Nippon Becton Dickinson Co., Ltd.) to culture the stem cells originating from a human fat, the cells stretched and proliferated in the state of a single layer and formed no cell aggregate (see FIG. 3).

[An Alkaline Phosphatase Activity]

Figure 4A:
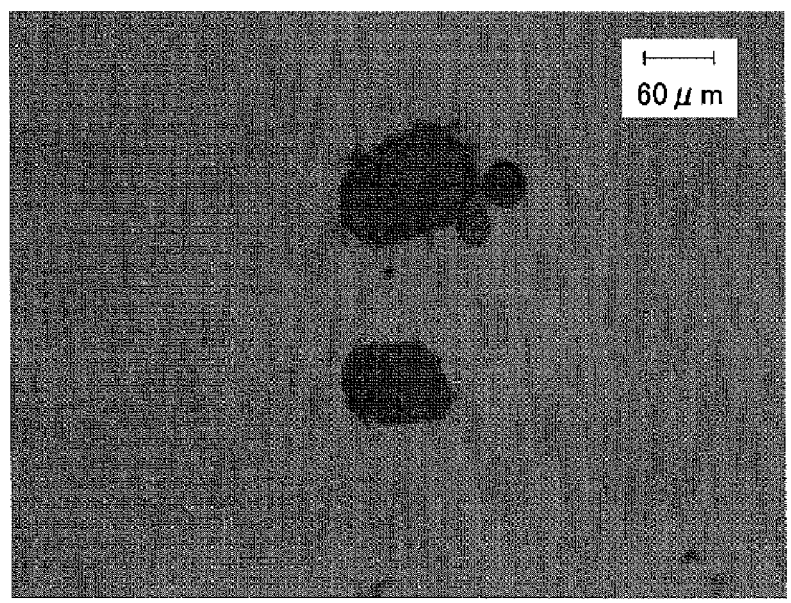
FIG. 4A is an optical micrograph illustrating an evaluation result of an alkaline phosphatase activity of a cell aggregate in practical example 1.
Figure 4B:
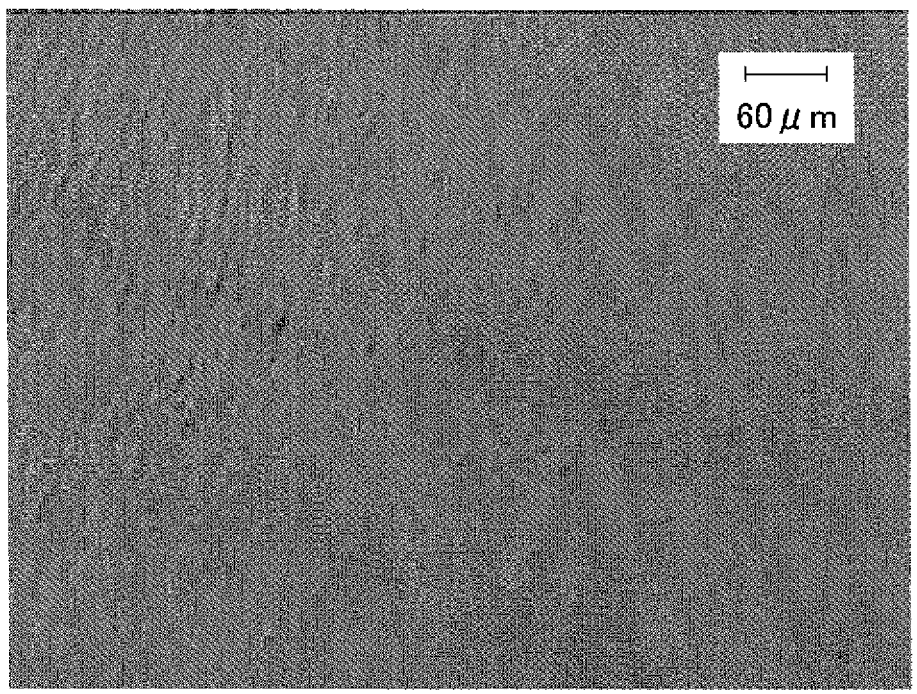
FIG. 4B is an optical micrograph illustrating an evaluation result of an alkaline phosphatase activity of a cell aggregate in comparative example 1.
Figure 5:
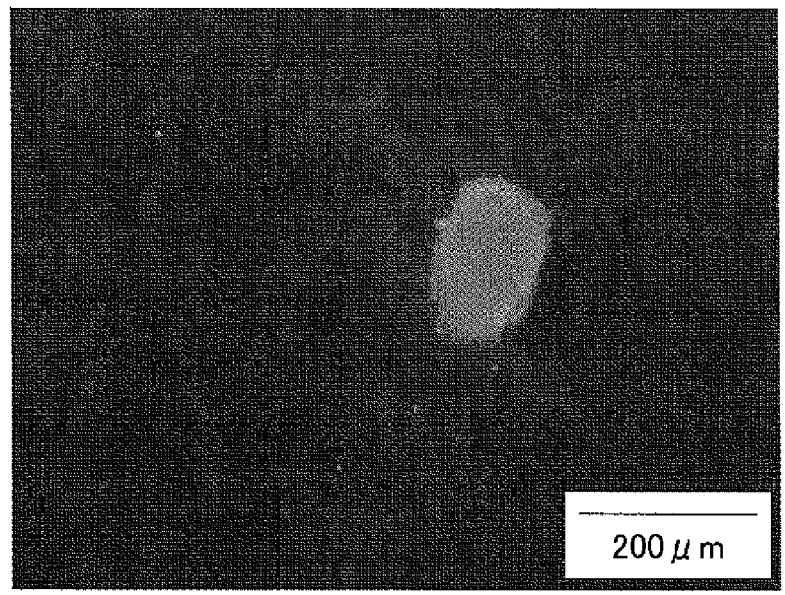
FIG. 5 is a fluorescence micrograph illustrating an evaluation result (part 1) of dual immunostaining of a cell aggregate in practical example 1.
Figure 5:
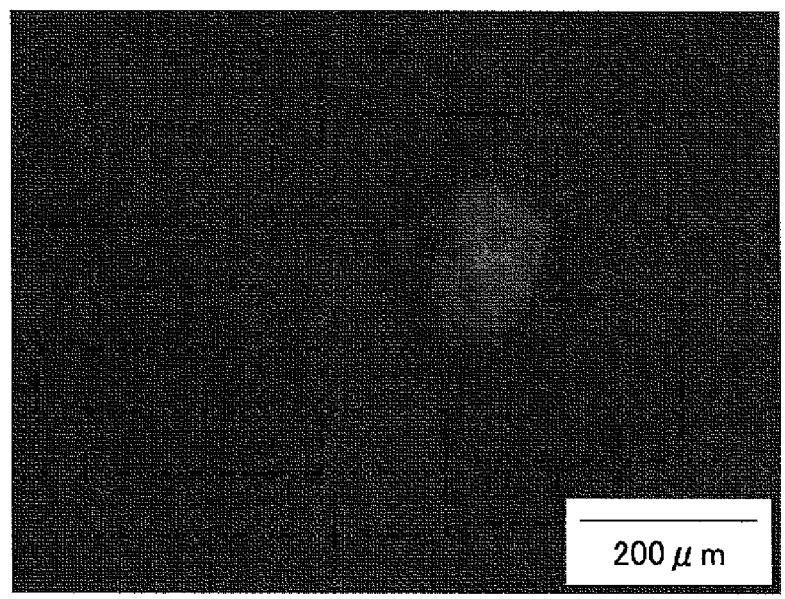
Figure 6:
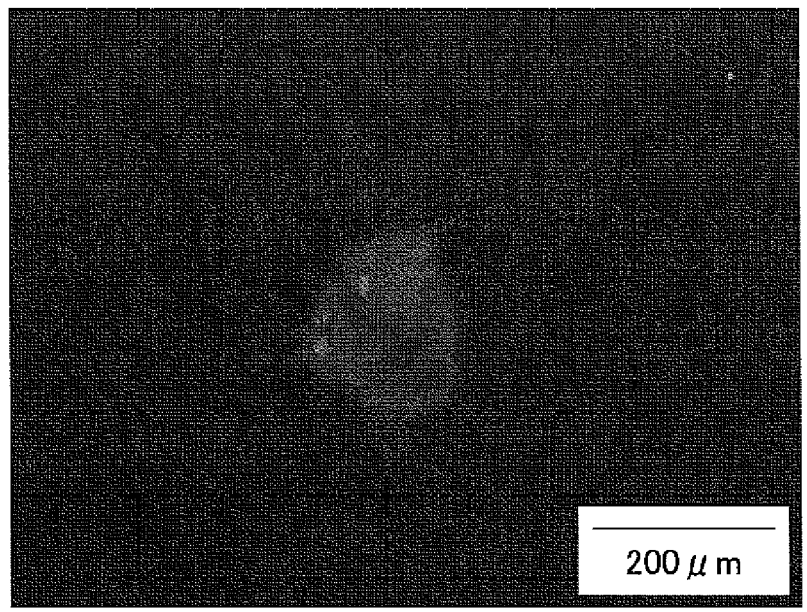
FIG. 6 is a fluorescence micrograph illustrating an evaluation result (part 2) of dual immunostaining of a cell aggregate in practical example 1.
Figure 6:
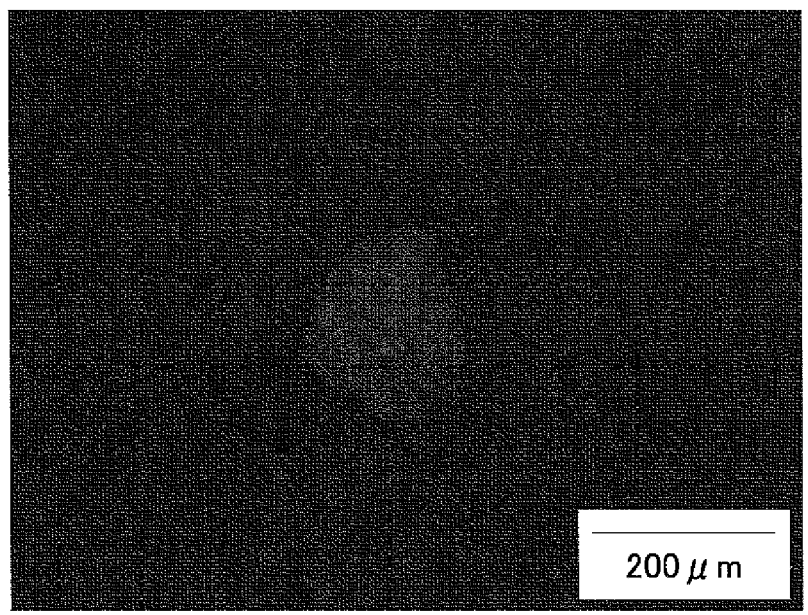
Figure 7:
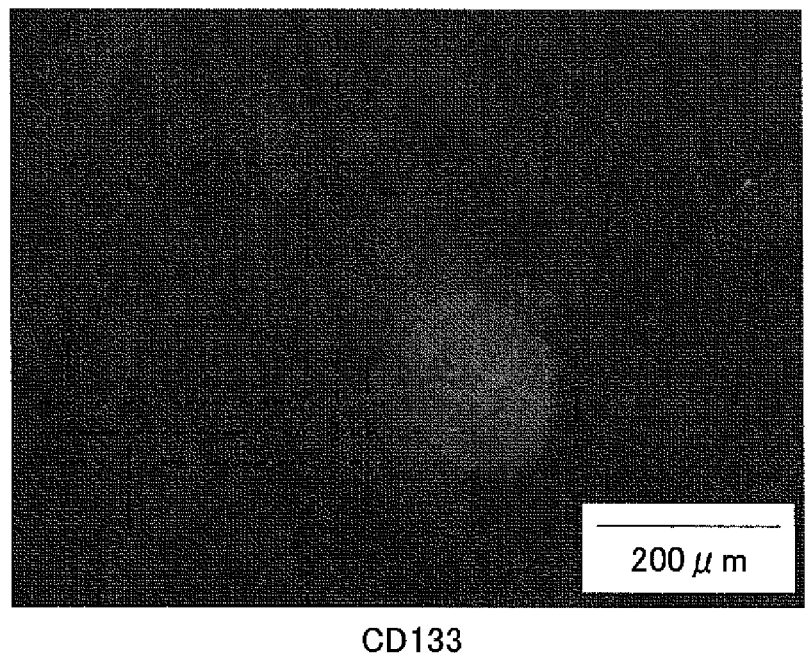
FIG. 7 is a fluorescence micrograph illustrating an evaluation result (part 3) of dual immunostaining of a cell aggregate in practical example 1.
Figure 7:
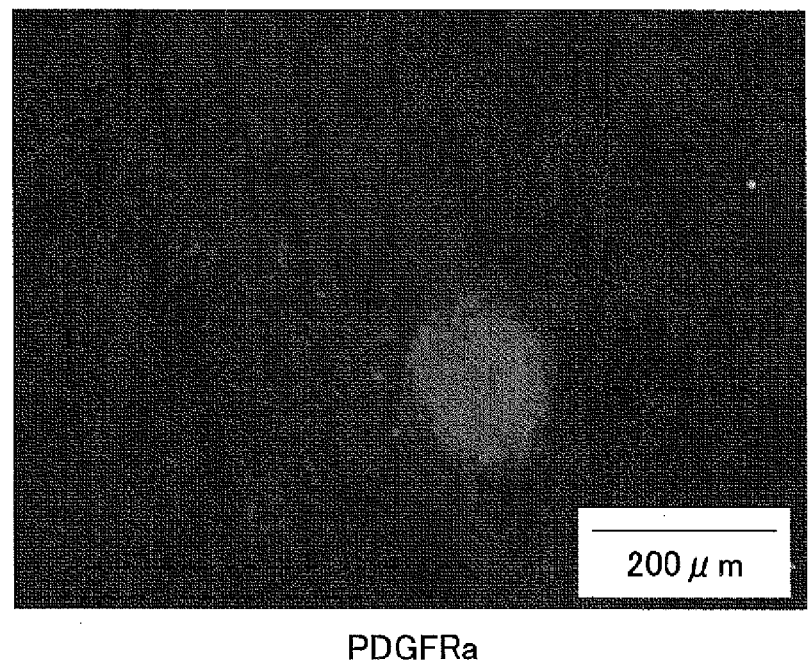
Figure 8:
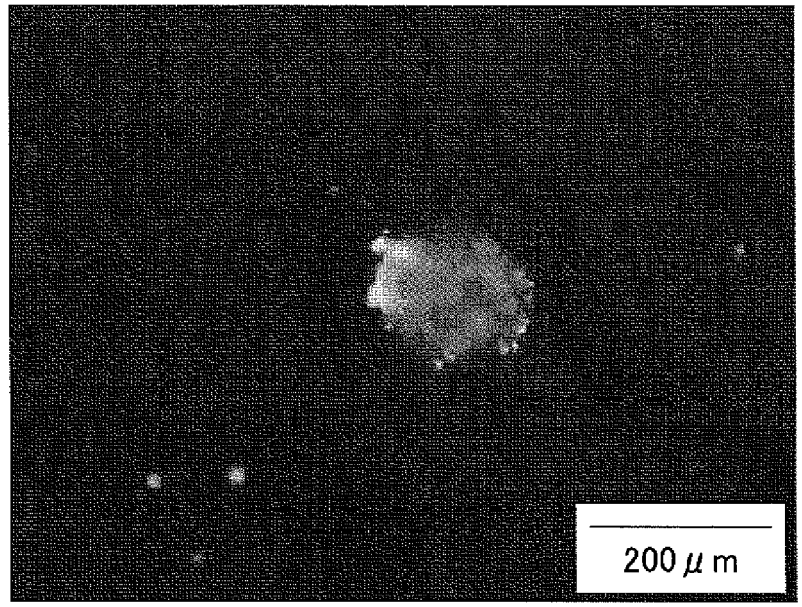
FIG. 8 is a fluorescence micrograph illustrating an evaluation result (part 4) of dual immunostaining of a cell aggregate in practical example 1.
Figure 8:
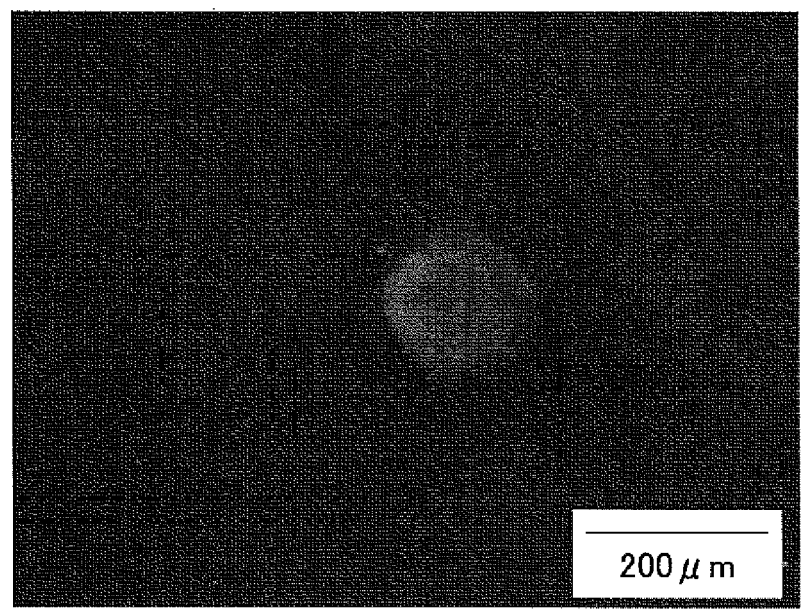

After a 4% by mass paraformaldehyde-phosphate buffer was added to a cell aggregate in practical example 1 and a cultured cell in comparative example 1 to conduct treatment thereof for 5 minutes, washing was conducted by using a TBS buffer and a TEST buffer. Then, after a BM Purple AP Substrate (produced by Roche Diagnostics Corporation) was added thereto and a reaction was conducted at 37° C. for 1 hour, washing was conducted by using a TBST buffer. Evaluation results were illustrated in FIGS. 4A and 4B. It can be seen from FIG. 4A and FIG. 4B that a cell aggregate in practical example 1 was positive for an alkaline phosphatase activity thereof whereas a cultured cell in comparative example 1 was negative for an alkaline phosphatase activity thereof.

[Dual Immunostaining]

After a 4% by mass paraformaldehyde-phosphate buffer was added to a cell aggregate in practical example 1 and a cultured cell in comparative example 1 to conduct treatment thereof for 5 minutes, washing was conducted by using a TBS buffer and a TBST buffer. Then, after a first primary antibody was diluted in accordance with a method described in a catalogue thereof and reacted with the cells, a first Alexa Fluor-labeled secondary antibody (produced by Invitrogen Corporation) was reacted with the cells and washing was conducted by using a TBST buffer. Furthermore, after a second primary antibody was diluted in accordance with a method described in a catalogue thereof and reacted with the cells, a second Alexa Fluor-labeled secondary antibody (produced by Invitrogen Corporation) was reacted with the cells and washing was conducted by using a TBST buffer. Evaluation results are illustrated in table 1.

TABLE 1

|  | Practical example 1 | Comparative example 1 |
| --- | --- | --- |
| Nestin | Positive | Negative |
| CD271 | High | Low |
| CD133 | Positive | Negative |

TABLE 1-continued

|  | Practical example 1 | Comparative example 1 |
| --- | --- | --- |
| PDGFRa | High | Low |
| PDGFRb | High | Low |

Herein, Nestin (produced by Abcam PLC), CD271 (produced by Abcam PLC), and CD133 (produced by Abcam PLC) are a marker for a stem cell originating from a nerve, a marker for a stem cell originating from a fat, and a marker for a stem cell, respectively, and PDGFRa (produced by R&D Co., Ltd.) and PDGFRb (produced by R&D Co., Ltd.) are markers for a mesenchymal stem cell. Furthermore, evaluation results of the cell aggregate in practical example 1 are illustrated in FIGS. 5-8. It can be seen from Table 1 that the cell aggregate in practical example 1 was Nestin-positive, and accordingly, the stem cell originating from a fat could acquire a property of a stem cell originating from a nerve in vitro.

Practical Example 2

An application liquid composed of 0.5 mL of a 0.15 mol/L solution of 3-aminopropyltrimethoxysilane in methanol, 9.5 mL of a 0.15 mol/L solution of a compound (A) represented by a chemical formula of:

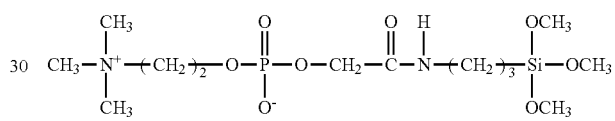

in methanol, and 10 mL of methanol was obtained.

The obtained application liquid was applied to a glass bottom dish (produced by Matsunami Glass Ind., Ltd.) and dried at room temperature. Then, after drying by heating and drying at room temperature were conducted, washing with water and drying were conducted to obtain a container for forming a cell aggregate.

Figure 9:
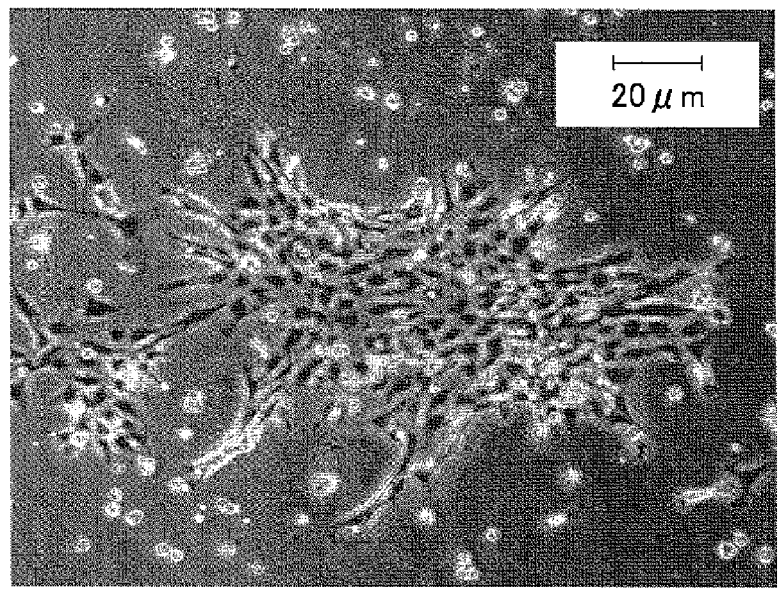
FIG. 9 is an optical micrograph illustrating a cell aggregate in practical example 2 (in a case of culturing for 7 days).

When 2.5 ml of a MensenPRO RS culture medium (produced by Invitrogen Corporation) and 1×10⁵/container of stem cells originating from a human fat (produced by Invitrogen Corporation) were added into the container for forming a cell aggregate to culture the stem cells originating from a human fat, the cells proliferated and formed a cell aggregate (see FIG. 9).

Practical Example 3

An application liquid composed of 7 mL of 0.15 mol/L solution of 3-aminopropyltrimethoxysilane in methanol, 3 mL of 0.15 mol/L solution of compound (A) in methanol, and 10 mL of methanol was obtained.

The obtained application liquid was applied to a glass bottom dish (produced by Matsunami Glass Ind., Ltd.) and dried at room temperature. Then, after drying by heating and drying at room temperature were conducted, washing with water and drying were conducted to obtain a container for forming a cell aggregate.

Figure 10:
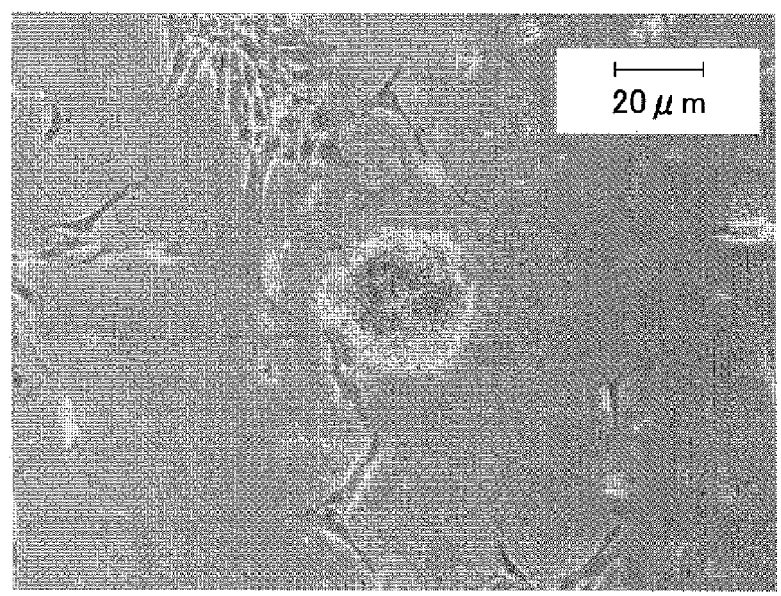
FIG. 10 is an optical micrograph illustrating a cell aggregate in practical example 3 (in a case of culturing for 7 days).

When 2.5 ml of a MensenPRO RS culture medium (produced by Invitrogen Corporation) and 1×10⁵/container of stem cells originating from a human fat (produced by Invitrogen Corporation) were added to the container for forming a cell aggregate to culture the stem cells originating from a human fat, the cells proliferated and formed a cell aggregate (see FIG. 10).

Comparative Example 2

Figure 11:
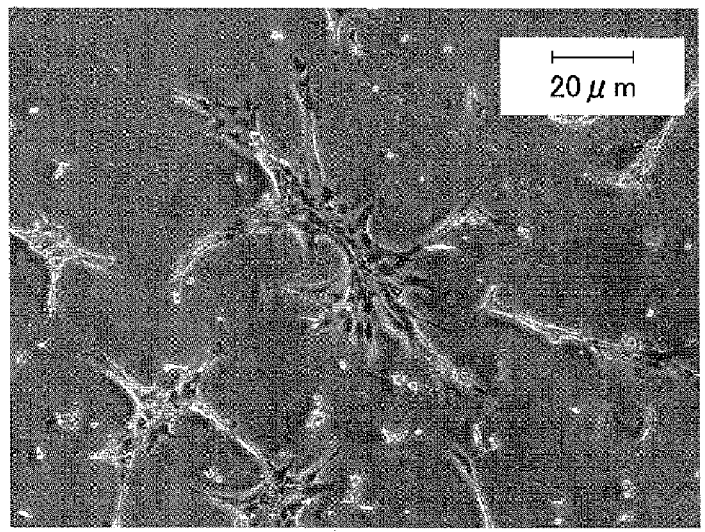
FIG. 11 is an optical micrograph illustrating a cultured cell in comparative example 2 (in a case of culturing for 7 days).

When 2.5 ml of a MensenPRO RS culture medium (produced by Invitrogen Corporation) and 1×10⁵/dish of stem cells originating from a human fat (produced by Invitrogen Corporation) were added to a glass bottom dish subjected to no surface treatment (produced by Matsunami Glass Ind., Ltd.) to culture the stem cells originating from a human fat, the cells stretched and proliferated in the state of a single layer and formed no cell aggregate (see FIG. 11).

[Immunostaining]

Figure 12:
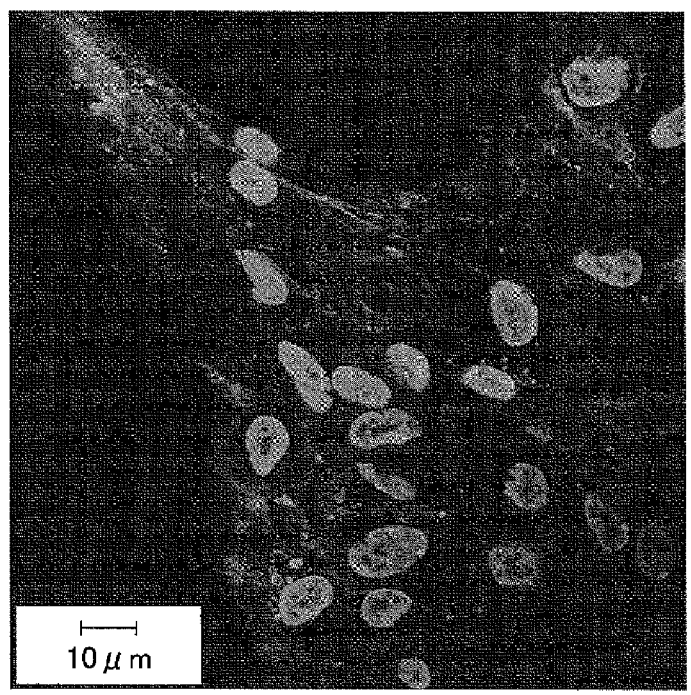
FIG. 12 is a photograph illustrating an evaluation result of immunostaining of a cell aggregate in practical example 2.

After a 4% by mass paraformaldehyde-phosphate buffer was added to cultured cells in the cell aggregate in practical example 2 for conducting treatment thereof for 5 minutes, washing was conducted by using a 0.2% by mass Triton X-100 (produced by produced by Roche Diagnostics Corporation)/TBS buffer and 0.2% by mass Tween 20 (produced by Tokyo Chemical Industry Co., Ltd.)/TBS buffer. Then, a non-specific reaction was blocked by Protein Block (produced by DAKO Corporation). Furthermore, after an anti-CD271 rabbit polyclonal antibody which was a primary antibody diluted 200 times (produced by Abeam PLC) and a CD90 mouse monoclonal antibody (produced by Abcam PLC) were reacted with the cells overnight, washing was conducted by using a 0.2% by mass Tween 20 (produced by Tokyo Chemical Industry Co., Ltd.)/TBS buffer. Then, after an Alexa 488 anti-rabbit antibody (produced by Invitrogen Corporation) and Alexa 594 anti-mouse antibody (produced by Invitrogen Corporation) which were fluorescent secondary antibodies diluted 250 times and capable of developing a green color and a red color, respectively, were reacted with the cells for 2 hours, washing was conducted by using a 0.2% by mass Tween 20 (produced by Tokyo Chemical Industry Co., Ltd.)/TBS buffer. Moreover, after a nucleus was stained with a Vectorshield-DAPI which was capable of developing a blue color (produced by Vector Corporation), observation was conducted by using a confocal laser microscope LSM 5 PASCAL (produced by Carl Zeiss). As a result, it could be seen that the cell aggregate in practical example 2 developed a green color, and accordingly, was positive for CD271 (see FIG. 12).

In addition, the cell aggregate in practical example 3 also developed a green color similarly to the cell aggregate in practical example 2, and accordingly, was positive for CD271.

APPENDIX

A Container for Forming a Cell Aggregate and a Method for Forming a Cell Aggregate The present invention aims at providing a container for forming a cell aggregate capable of forming a cell aggregate of adherent cells and a method for forming a cell aggregate by using the container for forming a cell aggregate, while a problem possessed by the above-mentioned conventional art is taken into consideration. Furthermore, the present invention aims at providing a method for screening a substance and method for exploring a cell function by using the method for forming a cell aggregate.

The invention as recited in embodiment (1) is a container for forming a cell aggregate, characterized in that a group represented by a general formula of:

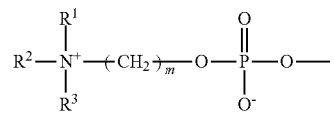

(in the formula, each of $R^1$, $R^2$, and $R^3$ is independently an alkyl group with a carbon number of 1 or more and 6 or less and m is an integer of 2 or more and 6 or less.) and at least one of an amino group, a carboxyl group, and a hydroxyl group are present near a surface thereof.

The invention as recited in embodiment (2) is the container for forming a cell aggregate as recited in embodiment (1), characterized by being manufactured by reacting a compound having a functional group having a reactivity with a carboxyl group, an amino group, or a hydroxyl group, a group represented by the general formula, and a molecular weight of 225 or more and 650 or less, with a container in which a carboxyl group, an amino group, and a hydroxyl group are present near a surface thereof.

The invention as recited in embodiment (3) is the container for forming a cell aggregate as recited in embodiment (2), characterized in that the container in which a carboxyl group, an amino group, and a hydroxyl group are present near a surface thereof is plasma-treated with under an atmosphere including at least one of oxygen, ozone, and a water vapor, and ammonia and/or nitrogen.

The invention as recited in embodiment (4) is the container for forming a cell aggregate as recited in embodiment (1), characterized by being manufactured by reacting a first compound having a functional group capable of producing a silanol group through hydrolysis thereof, a group represented by the general formula, and a molecular weight of 315 or more and 650 or less, and a second compound having a functional group capable of producing a silanol group through hydrolysis thereof and at least one of an amino group, a functional group capable of producing a carboxyl group through hydrolysis thereof, and a functional group capable of producing a hydroxyl group through hydrolysis thereof, with a container in which at least one of a functional group capable of producing a silanol group through hydrolysis thereof, a silanol group, a hydroxyl group originating from a semimetal oxide, and a hydroxyl group originating from a metal oxide is present near a surface thereof.

The invention as recited in embodiment (5) is the container for forming a cell aggregate as recited in embodiment (1), characterized in that a layer including a resin having a group represented by the general formula and at least one of an amino group, a carboxyl group, and a hydroxyl group is formed on a surface thereof.

The invention as recited in embodiment (6) is a method for forming a cell aggregate, characterized in that a somatic cell is cultured by using the container for forming a cell aggregate as recited in any one of embodiments (1) to (5) to form a cell aggregate.

The invention as recited in embodiment (7) is the method for forming a cell aggregate as recited in embodiment (6), characterized in that the somatic cell is an adherent cell.

The invention as recited in embodiment (8) is a method for screening a substance, characterized by including a step of culturing a somatic cell by using the container for forming a cell aggregate as recited in any one of embodiments (1) to (5) to form a cell aggregate and a step of screening a substance by using the cell aggregate.

The invention as recited in embodiment (9) is the method for screening a substance as recited in embodiment (8), characterized in that the somatic cell is an adherent cell.

The invention as recited in embodiment (10) is a method for exploring a cell function, characterized by including a step of culturing a somatic cell by using the container for forming a cell aggregate as recited in any one of embodiments (1) to (5) to form a cell aggregate and a step of exploring a cell function by using the cell aggregate.

The invention as recited in embodiment (11) is the method for exploring a cell function as recited in embodiment (10), characterized in that the somatic cell is an adherent cell.

According to the present invention, it is possible to provide a container for forming a cell aggregate capable of forming a cell aggregate of adherent cells and a method for forming a cell aggregate by using the container for forming a cell aggregate. Furthermore, according to the present invention, it is possible to provide a method for screening a substance and method for exploring a cell function by using the method for forming a cell aggregate.

The present international application claims the priority based on Japanese Patent Application No. 2009-142254 filed on Jun. 15, 2009 and the entire content of Japanese Patent Application No. 2009-142254 is incorporated by reference in the present international application.

EXPLANATION OF LETTERS OR NUMERALS

C An adherent cell
D A container for forming a cell aggregate
The invention claimed is:

1. A container for forming a cell aggregate,
wherein the container is manufactured by reacting
a compound including
a functional group, and
a group represented by a general formula of:

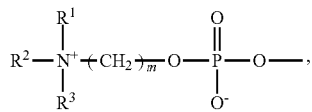

wherein each of $R^1$, $R^2$, and $R^3$ is independently an alkyl group with a carbon number of 1 or more and 6 or less and m is an integer of 2 or more and 6 or less, wherein a molecular weight of the compound is 225 or more and 650 or less, with
an unreacted container with a carboxyl group, an amino group, and a hydroxyl group on a surface thereof;
a) wherein the functional group of the compound has a reactivity with a carboxyl group and is an amino group or a hydroxyl group so that a condensation reaction between an amino group or a hydroxyl group of the compound and a carboxyl group on the surface of the unreacted container occurs, and at least an amino group and a hydroxyl group of the unreacted container are left on the surface of the container, or
b) wherein the functional group of the compound has a reactivity with an amino group or a hydroxyl group and is a carboxyl group or an aldehyde group so that a condensation reaction between a carboxyl group or an aldehyde group of the compound and an amino group or a hydroxyl group on the surface of the unreacted container occurs, and, for part b), at least a carboxyl group of the unreacted container is left on the surface of the container.

2. The container for forming a cell aggregate as claimed in claim 1, wherein the unreacted container is plasma-treated with under an atmosphere including at least one of oxygen, ozone, and a water vapor, and ammonia and/or nitrogen.

3. A container for forming a cell aggregate,
wherein the container is manufactured by reacting
a first compound having
a first alkoxysilyl group that is a functional group capable of producing a silanol group through hydrolysis thereof, and
a group represented by a general formula of:

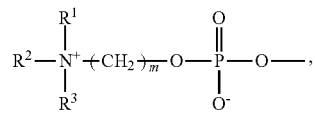

wherein each of $R^1$, $R^2$, and $R^3$ is independently an alkyl group with a carbon number of 1 or more and 6 or less and m is an integer of 2 or more and 6 or less, wherein a molecular weight of the first compound is 315 or more and 650 or less, and
a second compound having a second alkoxysilyl group that is a functional group capable of producing a silanol group through hydrolysis thereof and an amino group, with
an unreacted container with silanol groups on a surface thereof,
to cause at least
a condensation reaction between a silanol group produced by hydrolysis of the first alkoxysilyl group of the first compound and a silanol group on the surface of the unreacted container and
a condensation reaction between a silanol group produced by hydrolysis of the second alkoxysilyl group of the second compound and a silanol group on the surface of the unreacted container,
so that the group represented by a general formula of the first compound and an amino group of the second compound is present on the surface of the container.

* * * * *